United States Patent [19]

Fischer

[11] Patent Number: 4,822,946

[45] Date of Patent: Apr. 18, 1989

[54] PREPARATION OF OLEFINS FROM TERTIARY ALKYL HALIDES

[75] Inventor: Martin Fischer, Ludwigshafen, Fed. Rep. of Germany

[73] Assignee: BASF Aktiengesellschaft, Ludwigshafen, Fed. Rep. of Germany

[21] Appl. No.: 158,614

[22] Filed: Feb. 22, 1988

[30] Foreign Application Priority Data

Mar. 12, 1987 [DE] Fed. Rep. of Germany ....... 3707903

[51] Int. Cl.$^4$ .............................................. C07C 1/00
[52] U.S. Cl. .................................................. 585/641
[58] Field of Search ......................................... 585/641

[56] References Cited

U.S. PATENT DOCUMENTS

| | | | |
|---|---|---|---|
| 1,198,944 | 9/1916 | Matthews et al. | 585/641 X |
| 3,341,615 | 9/1967 | Wulf et al. | 585/641 X |

FOREIGN PATENT DOCUMENTS

| | | | |
|---|---|---|---|
| 1568073 | 4/1970 | Fed. Rep. of Germany . | |
| 1363492 | 12/1964 | France | 585/641 X |
| 17234 | 7/1913 | United Kingdom | 585/641 X |
| 989254 | 4/1965 | United Kingdom | 585/641 X |
| 1142718 | 2/1969 | United Kingdom | 585/641 X |

OTHER PUBLICATIONS

Houben–Weyl, Methoden der organischen Chemie, vol. V, part 1b, pp. 134–135, 170.
J. American Chem. Soc. vol. 75 (1953), pp. 10–14.

Primary Examiner—Patrick P. Garvin
Assistant Examiner—George R. Fourson
Attorney, Agent, or Firm—John H. Shurtleff

[57] ABSTRACT

A process for the preparation of olefins by the elimination of hydrogen halide from tertiary alkyl halides, the reaction being carried out by heating the alkyl halide in water to from 40° to 130° C. and simultaneously distilling off from the reaction mixture the olefins formed.

4 Claims, No Drawings

PREPARATION OF OLEFINS FROM TERTIARY ALKYL HALIDES

The present invention relates to a novel process for the preparation of olefins by the elimination of hydrogen halide from tertiary alkyl halides.

It is known that tertiary alkyl halides can be converted into olefins by the elimination of hydrogen halide. There are various ways of carrying out this reaction: for instance, elimination of hydrogen halide can be brought about by treating the tertiary alkyl halide with basic reagents or subjecting it to pyrolysis or solvolysis—see Houben-Weyl, Methoden der organischen Chemie, vol. V, part 1b, pp. 134–5 (1972).

In the elimination of hydrogen halide by means of basic reagents such as alkali alkoxides or tertiary amines stoichiometric amounts of the bases are consumed. In solvolysis the hydrogen halide eliminated is not bound chemically and does not use up an expensive reactant. This advantage is however counterbalanced by the fact that the olefin yield is unsatisfactory, owing to competing substitution reactions, and distinctly worse than that given by treatment with bases, where the mechanism is bimolecular, in distinction to unimolecular solvolysis—see S. Patai, The Chemistry of Alkenes, p. 181(1964). Solvolysis of tertiary alkyl halides is usually carried out in mixtures of organic solvents such as ethanol, dioxan, or acetone with water. A 4:1 mixture of ethanol and water is used most frequently—cf. J. Am. Chem. Soc., 75, 10–14 (1953).

We have now found that in the preparation of olefins of the general formulae I and II—where $R^1$, $R^2$, $R^3$, $R^5$, and $R^6$ are hydrogen atoms or alkyl groups of from 1 to 6 carbon atoms and $R^4$ is an alkyl group with from 1 to 6 carbon atoms or a phenyl

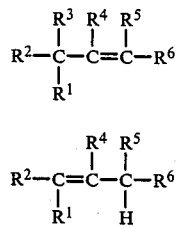

group, which may be substituted by an alkyl group, an alkoxy group, or a halogen atom—by elimination of hydrogen halide from tertiary alkyl halides of the general formula III—where $R^1$ to $R^6$ are as given above and X is a chlorine or bromine atom—, the molecular weight of the latter being not more than 280, the yields are particularly good if the reaction is carried out by heating the alkyl halide in water to a temperature of from 40° C. to 130° C., the olefins formed being removed continually from the reaction mixture by distillation.

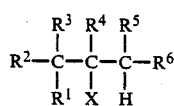

This advantageous result is surprising, since according to Houben-Weyl, Methoden der organischen Chemie, vol. V, part 1b, p. 170 (1972) the olefin yield from the known solvolysis reaction decreases with increase in water content in alcoholic reaction media.

The substituent alkyl groups in the tertiary alkyl halides of the general formula III may have from 1 to 6 carbon atoms, but groups with from 1 to 4 carbon atoms, such as ethyl, propyl, isopropyl, butyl, or isobutyl, are preferred. The group $R^4$ can be phenyl or phenyl substituted by alkyl groups such as methyl or ethyl, alkoxy groups such as methoxy, or halogen atoms such as chlorine or bromine.

The following are examples of suitable alkyl halides: tert-amyl chloride, tert-amyl bromide, tert-butyl chloride, cumyl chloride, cumyl bromide, 4-methylcumyl chloride.

The novel process is carried out in an aqueous medium. For instance, the alkyl halide of general formula III is added to water, in which it is not soluble, in the mass ratio of from 0.2:1 to 2.5:1. While the mixture is being heated the olefin is distilled off as it is formed. A greater or smaller part of the water also distils over as an azeotrope while the process is being carried out, depending on the boiling point of the olefin or mixture of olefins formed by elimination of hydrogen halide. The water and olefins that distil over can be separated easily by separating the liquid phases.

The hydrogen halide eliminated from the alkyl halide dissolves in the water in the reaction vessel. When the mass concentration of acid reaches 20% the formation of olefin becomes noticeably slower. It is expedient to stop the reaction when the saturation concentration of acid is reached in the reaction mixture. If at this point not all of the alkyl halide has reacted the aqueous acid solution can be drawn off and replaced by water, which causes elimination of hydrogen halide to start again.

To prevent part of the alkyl halide from distilling over with the olefin or olefins that are formed it is advisable to interpose a column, with from two to six plates for instance, between the reaction vessel and the condenser; this will hold back unreacted alkyl halide.

The reaction temperature depends on the boiling points of the alkyl halide used and the olefin or mixture of olefins that distils off. It is practical to adjust it to from 10 K. to 60 K. above the boiling point of the olefins formed or the temperature of their azeotrope with water.

The reaction can be carried out under pressures from 0.3 bar to 5 bar. The least technical resources are required if the reaction is carried out at atmospheric pressure or pressures slightly above or below it. The novel process can be carried out continuously or batchwise. In an advantageous embodiment of the invention the water in the reaction vessel is heated to the required temperature and the alkyl halide is metered in at a rate equivalent to that at which the olefin or olefins formed distil over. In batchwise production the charges usually require reaction times of from 1 h to 12 h. Longer reaction times do not impair the yield, and can be tolerated, for instance when the olefin cannot be distilled off quickly.

In the novel process the elimination of hydrogen halide takes place in water; addition of solvent is not necessary, but it is possible. Since hydrogen halide is set free in the reaction and forms a solution of the corresponding acid in the aqueous reaction medium, it is possible to start with dilute aqueous solution of the acid. Thus the aqueous reaction medium may be water or an aqueous mixture with hydrogen halides or solvents.

The mass fraction of solvent in the aqueous medium can be, for example, from 0% to 70%, preferably from 0% to 40%, above all from 0% to 10%; the mass fraction of hydrogen halide can be from 0% to 15%, preferably from 0% to 5%. Suitable solvents are those that are resistant to hydrogen halides under the conditions of the reaction, and include toluene, chloroform, dichloroethane, and methylene chloride.

EXAMPLE 1

In a flask fitted with a stirrer 500 ml of water is heated to a temperature of from 65° C. to 70° C. In the course of 6 h 586 g of tert-amyl chloride is added dropwise, the olefins formed being distilled off continuously through a 30-cm column packed with 5-mm glass ring; the head temperature is not allowed to exceed 38° C. The distillate consists of 14 ml of water and 354 g of a mixture of olefins containing 90% 2-methyl-2-butene and 10% 2-methyl-1-butene.

EXAMPLE 2

In a flask fitted with a stirrer and a reflux condenser to which a cold trap is connected 300 ml of water is heated to a temperature of from 50° C. to 55° C. 50 g of tert-butyl chloride is added dropwise, the mixture being kept boiling under reflux. After an hour 2-methyl-1-propene (isobutylene) begins to collect in the trap, which is cooled to −70° C. The induction phase leading up to the formation of the olefin can be obviated by the addition of 10 ml of concentrated hydrochloric acid. Over a period of 6 h 100 g more of tert-butyl chloride is added dropwise. Altogether 82 g of isobutylene collects in the cold trap.

EXAMPLE 3

In a flask fitted with a stirrer 500 ml of water is heated to 110° C., and 250 g of cumyl chloride is added dropwise over a period of 6 h. Continuous distillation is carried out through the column described in Example 1, yielding 166 g of alpha-methylstyrene and 190 ml of water.

I claim:

1. A process for the preparation of olefins of the formulae

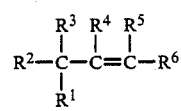

and

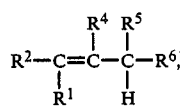

where $R^1$, $R^2$, $R^3$, $R^5$ and $R^6$ are hydrogen atoms or alkyl groups with from 1 to 6 carbon atoms and $R^4$ is an alkyl group with from 1 to 6 carbon atoms, by elimination of hydrogen halide from tertiary alkyl halides of the formula

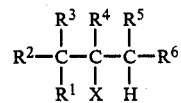

where $R^1$ to $R^6$ are as given above and X is a chlorine or bromine atom, whose molecular weight does not exceed 280, the reaction being carried out by heating the alkyl halide suspended in water, as an aqueous reaction mixture substantially free of alcohols, to a temperature of from 40° C. to 130° C., and the olefins formed being removed continually from the reaction mixture by distillation.

2. A process as claimed in claim 1 wherein the ratio of the mass of alkyl halide to the mass of water is from 0.2:1 to 2.5:1.

3. A process as claimed in claim 1 wherein the reaction is carried out under a pressure of from 0.3 bar to 5 bar.

4. A process a claimed in claim 1 wherein the alkyl halide is tert-amyl chloride or tert-butyl chloride.

* * * * *